United States Patent [19]

Hofmeister et al.

[11] Patent Number: 4,464,365
[45] Date of Patent: Aug. 7, 1984

[54] 11β-CHLORO-Δ15-STEROIDS, A PROCESS FOR THEIR PREPARATION AND PHARMACEUTICAL PREPARATIONS CONTAINING THEM

[75] Inventors: Helmut Hofmeister; Karl Petzoldt; Klaus Annen; Henry Laurent; Rudolf Wiechert; Yukeshige Nishino, all of Berlin, Fed. Rep. of Germany

[73] Assignee: Schering Aktiengesellschaft, Berlin & Bergkamen, Fed. Rep. of Germany

[21] Appl. No.: 485,800

[22] Filed: Apr. 18, 1983

[30] Foreign Application Priority Data

Apr. 16, 1982 [DE]  Fed. Rep. of Germany ....... 3214690

[51] Int. Cl.³ ............................................. A61K 31/56
[52] U.S. Cl. .................................. 424/243; 260/397.45
[58] Field of Search ................... 260/397.45; 424/243

[56] References Cited

U.S. PATENT DOCUMENTS 3,933,799  1/1976  Phillipps ........................ 260/397.45
4,081,537  3/1978  Hofmeister et al. ........... 260/397.45

FOREIGN PATENT DOCUMENTS 7209299  1/1974  Netherlands ................... 260/397.45

Primary Examiner—Elbert L. Roberts
Attorney, Agent, or Firm—Millen & White

[57] ABSTRACT

11β-Chloro-Δ15-steroids of Formula I

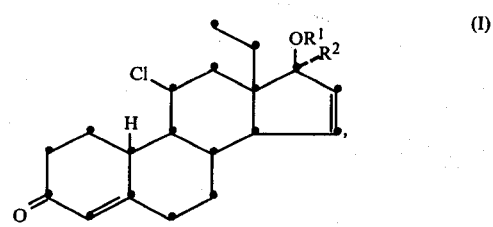

wherein
R¹ is hydrogen or acyl and
R² is ethynyl, chloroethynyl, or propynyl have strong progestational activity.

19 Claims, No Drawings

11β-CHLORO-Δ¹⁵-STEROIDS, A PROCESS FOR THEIR PREPARATION AND PHARMACEUTICAL PREPARATIONS CONTAINING THEM

BACKGROUND OF THE INVENTION

The present invention relates to 11β-chloro-Δ¹⁵-steroids, a process for their preparation, and pharmaceutical preparations containing them.

It has been known that 11β-chloro steroids possess valuable biological properties. For example, Dutch Laid-Open Application No. 7209299 describes 11β-chloro-17α-ethynyl-18-methyl-4-estrenes having a strong progestational activity. However, such compounds have disadvantages.

SUMMARY OF THE INVENTION

Accordingly, it is an object of this invention to provide new compounds having valuable pharmacological properties.

Upon further study of the specification and appended claims, further objects and advantages of this invention will become apparent to those skilled in the art.

These objects have been attained by providing 11β-Chloro-Δ¹⁵-steroids of Formula I

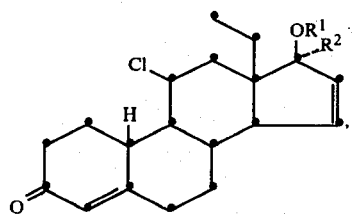

wherein
$R^1$ is hydrogen or an acyl group and
$R^2$ is ethynyl, chloroethynyl, or propynyl.

Detailed Discussion

The acyl groups $R^1$ in Formula I are derived from acids customarily employed for esterifications in steroid chemistry. Preferred acids are organic carboxylic acids usually hydrocarbon based of up to 15 carbon atoms, especially lower and intermediate aliphatic carboxylic acids of up to 7 carbon atoms, e.g., $C_{1-15}$ or $C_{1-7}$-alkanoic acids. Contemplated equivalents include such acids which are unsaturated, branched, polybasic, or substituted in the usual way, for example by hydroxy, acyloxy, alkoxy, oxo, or amino groups or by halogen atoms, as well as cycloaliphatic, aromatic, mixed aromatic-aliphatic, and heterocyclic acids which can also be substituted as usual.

Examples include the following carboxylic acids: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, β-cyclopentylpropionic acid, cyclohexylacetic acid, cyclohexanecarboxylic acid, phenylacetic acid, phenoxyacetic acid, mono-, di-, and trichloroacetic acids, aminoacetic acid, diethylaminoacetic acid, piperidinoacetic acid, morpholinoacetic acid, lactic acid, O-tridecanoylglycolic acid, succinic acid, adipic acid, benzoic acid, nicotinic acid, isonicotinic acid, furan-2-carboxylic acid, etc.

The novel 11β-chloro-Δ¹⁵-steroids of Formula I can be produced by introduction of the $R^2$ residue into 17-oxo steroids of Formula II, i.e., by according to conventional methods, introducing the residue $R^2$ at the $C_{17}$-atom, of a 17-oxo steroid of Formula II

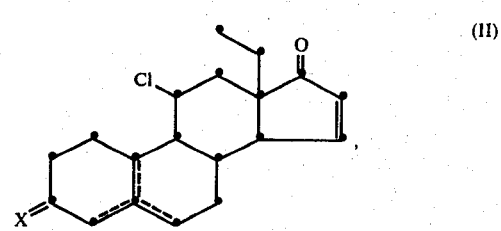

wherein
X is a free oxo group or an acid-hydrolyzable blocked oxo group and

is a double bond in the 4,5- 5,6- or 5,10-position, or two double bonds emanating from the 3- and 5-positions, using an agent which releases the residue $R^2$, thereby forming a tertiary carbinol; hydrolyzing the 3-oxo blocking group; and, depending on the finally desired value of $R^1$, optionally, esterifying the 17-hydroxy group prior to or after splitting off the oxo blocking group.

The introduction of the residue $R^2$ can be effected according to conventional methods using an organometallic ethynyl, chloroethynyl, or propynyl compound. Such organometallic compounds include, for example, alkali metal acetylides, e.g. potassium and lithium acetylides, potassium and lithium chloroacetylides and/or potassium and lithium methylacetylides.

The organometallic compound can also be formed in situ and made to react with the 17-ketone of Formula II. Thus, it is possible, for example, to treat the 17-ketone in a suitable solvent with acetylene and an alkali metal, especially potassium, sodium, or lithium, in the presence of a $C_4$- or $C_5$-alcohol or ammonia, or in the form of butyllithium, for example. Lithium chloroacetylide can be obtained from 1,2-dichloroethylene and an ethereal alkali metal alkyl, especially methyllithium, solution.

Suitable organometallic ethynyl compounds also include ethynylmagnesium or ethynylzinc halides, particularly ethynylmagnesium bromide or iodide.

Especially suitable solvents are dialkyl ethers, tetrahydrofuran, dioxane, benzene, toluene, etc. The reaction takes place at temperatures of −78° C. to +50° C.

The optionally subsequent esterification of the 17-hydroxy group takes place according to methods customarily employed in steroid chemistry for the esterification of tertiary hydroxy groups. Suitable esterification methods include, for example, the reaction of the steroids with acid anhydrides or acid chlorides in the presence of alkaline catalysts, such as sodium bicarbonate, potassium bicarbonate, potassium carbonate, sodium hydroxide, potassium hydroxide, pyridine, lutidine, collidine, triethylamine, or 4-dimethylaminopyridine. According to a preferred embodiment, the esterification is conducted in the presence of pyridine and 4-dimethylaminopyridine.

The 3-oxo blocking group is hydrolyzed according to methods known to those skilled in the art; this step can be performed before or also after the possible esterification. Usable for purposes of the hydrolysis are mineral acids, e.g. perchloric acid, sulfuric acid, or hydrochloric acid, or organic acids, such as, for example, oxalic acid. The hydrolysis is preferably conducted in an alcoholic solution or in other polar solvents, e.g. acetone, at temperatures of about 20° to 100° C.

The oxo blocking group X in Formula II forms, with the double bond(s) present in the A or B ring, such an arrangement of atoms that the compound is converted, by acidic hydrolysis, into a 4,5-unsaturated 3-oxo steroid. According to a preferred embodiment, the 3-oxo group is blocked by ketal formation. The ketal residues are derived from the alcohols and thioalcohols usually employed for the blocking of free oxo groups; examples include: ethylene glycol, 2,2-dimethyl-1,3-propanediol, and 1,2-ethanedithiol. The 3-oxo group, however, can also be partially blocked by enol ether, enol ester, or enamine formation.

It has now been found that the novel 11$\beta$-chloro-$\Delta^{15}$-steroids of Formula I have at least three times the progestational activity of the 11$\beta$-chloro steroids known from Dutch Application No. 7209299.

The progestational activity was determined by the customary Clauberg test upon oral administration to infantile (immature) female rabbits.

The minimum quantity required to obtain a positive effect is expressed by a McPhail value of 1.5.

The following Table is a compilation of the test results.

TABLE

| Compound | Dose (mg) | McPhail |
|---|---|---|
| A 11$\beta$-Chloro-17$\alpha$-ethynyl- | 0.1 | 3.1 |
| 17$\beta$-hydroxy-18-methyl- | 0.03 | 2.9 |
| 4,15-estradien-3-one | 0.01 | 2.3 |
|  | 0.003 | 1.4 |
| B 11$\beta$-Chloro-17$\alpha$-ethynyl- | 0.03 | 2.5 |
| 17$\beta$-hydroxy-18-methyl- | 0.01 | 1.4 |
| 4-estren-3-one | 0.003 | 1.1 |

The table shows that the threshold dose (McPhail 1.5) for progestational activity is, in case of compound A of this invention, about 0.003 mg, and, in the conventional compound B, approximately 0.01 mg.

Due to their progestational effectiveness, the compounds of Formula I can be utilized, for example, in contraceptives where they are contained as the progestational components in combination with an estrogenically effective hormonal component, e.g. ethynylestradiol, or as the sole active component. The compounds can also be utilized, however, in preparations for the treatment of gynecological disturbances. Unless indicated otherwise herein, the use of the compounds of this invention for such purposes is fully conventional, e.g., analogously to that of the known progestogen norgestrel (U.S. Pat. No. 3,959,322).

The novel compounds can be processed together with the additives, excipients, and flavor-ameliorating agents customary in galenic pharmacy, into the customary pharmaceutical formulations in a manner known per se. Especially suitable for oral administration are tablets, dragees, capsules, pills, suspensions, or solutions. Suitable for parenteral administration are, in particular, oily solutions, e.g. sesame oil solutions or castor oil solutions, which can optionally contain a further diluent, e.g. benzyl benzoate or benzyl alcohol. The concentration of the active ingredient is dependent on the form of administration. Thus, tablets for oral administration, for example, contain preferably 0.01–0.5 mg of active agent, and solutions for parenteral administration contain preferably 1–100 mg of active agent per 1 ml of solution.

The dose of the medicines of this invention can vary conventionally with the dosage form and purpose of administration. For example, the daily contraceptive dose upon oral administration is 0.01–0.5 mg of the novel progestogen, optionally in combination with 0.01–0.05 mg of ethynylestradiol.

Dosages for a given host for a given indication can be determined, e.g., by customary comparison of the activities of the subject compound and of a known agent by means of an appropriate, conventional pharmacological protocol.

The starting compounds of general Formula II utilized according to the process of this invention can be produced from 11$\beta$-chloro-18-methyl-4-estrene-3,17-dione (Dutch Laid-Open Application No. 7209299) as follows:

11$\beta$-Chloro-15$\alpha$-hydroxy-18-methyl-4-estrene-3,17-dione

A 2-liter Erlenmeyer flask, containing 500 ml of a nutrient solution sterilized for 30 minutes at 120° C. in an autoclave and consisting of 3.0% glucose, 1.0% corn steep liquor, 0.2% NaNO$_3$, 0.1% KH$_2$PO$_4$, 0.2% K$_2$HPO$_4$, 0.05% MgSO$_4$.7H$_2$O, 0.002% FeSO$_4$.7H$_2$O, and 0.05% KCl, is inoculated with a slanted-tube culture of the strain Penicillium raistrickii (ATCC 10 490) and shake for 2½ days at 30° C. on a rotary shaker.

250 ml of this incubation culture is utilized for inoculating a 20-liter preliminary fermentor filled with 15 l of a medium of the same composition as the incubation culture, sterilized for 60 minutes at 121° C. and under 1.1 atm. gauge. With the addition of silicone SH as the defrother, germination is conducted for 24 hours at 29° C. and 0.7 atm. gauge pressure under aeration (15 l/min) and agitation (220 rpm).

Thereafter, 0.9 l of this preliminary fermentor culture is withdrawn under sterile conditions and used for inoculating a 20-liter main fermentor charged with 14 l of a nutrient medium sterilized as above and having the same composition as the preliminary fermentor culture. After an incubating phase of 12 hours under preliminary fermentor conditions, a solution of 2.6 g of 11$\beta$-chloro-18-methyl-4-estrene-3,17-dione in 130 ml of dimethylformamide is added and the mixture is further stirred and aerated. The progression of fermentation is controlled by withdrawing samples which are extracted by means of methyl isobutyl ketone and analyzed by thin-layer chromatography. After a contact period of 14 hours, the substrate reaction is completed. The culture broth is filtered, the filtrate is extracted three times with respectively 10 l of methyl isobutyl ketone, and the extracts are combined with the extract of the mycelium, likewise extracted with methyl isobutyl ketone. After concentrating the solution in a forced circulation evaporator, the mixture is concentrated to dryness at a bath temperature of 50° C. under vacuum with the use of a forced circulation evaporator. The oily-crystalline residue is chromatographed for purification purposes over a silica gel column and eluted with the solvent gradient of 5 l of methylene chloride/3.5 l of methylene chloride + 1.5 l of acetone. The main fraction (2.28 g) is finally recrystallized from methylene chloride/isopropyl ether, thus obtaining 1.8 g of pure 11β-chloro-15α-hydroxy-18-methyl-4-estrene-3,17-dione, mp 169°–170° C.

15α-Acetoxy-11β-chloro-18-methyl-4-estrene-3,17-dione 1.6 g of 11β-chloro-15α-hydroxy-18-methyl-4-estrene-3,17-dione in 5 ml of pyridine is stirred at room temperature under argon with 1.2 ml of acetic anhydride. After 18 hours, the solution is introduced into hydrochloric-acid-containing ice/water. The thus-precipitated product is vacuum-filtered, dissolved in ethyl acetate, and washed with water. Recrystallization of the crude product from isopropyl ether yields 1.0 g of 15α-acetoxy-11α-chloro-18-methyl-4-estrene-3,17-dione, mp 125.0° C.

15α-Acetoxy-11β-chloro-3,3-(2',2'-dimethyltrimethylenedioxy)-18-methyl-5-estren-17-one 1.3 g of 15α-acetoxy-11β-chloro-18-methyl-4-estrene-3,17-dione in 13 ml of methylene chloride and 1.3 ml of triethyl orthoformate are combined at room temperature with 2.5 g of 2,2-dimethyl-1,3-propanediol and 15 mg of p-toluenesulfonic acid. After 7 hours, the mixture is diluted with methylene chloride, washed with NaHCO$_3$ solution and water, and dried. Chromatography of the crude product on silica gel with hexane/acetone (0–20%) produces 800 mg of 15α-acetoxy-11β-chloro-3,3-(2',2'-dimethyltrimethylenedioxy)-18-methyl-5-estren-17-one, mp 191.5° C.

11β-Chloro-3,3-(2',2'-dimethyltrimethylenedioxy)-18-methyl-5,15-estradien-17-one 600 mg of 15α-acetoxy-11β-chloro-3,3-(2',2'-dimethyltrimethylenedioxy)-18-methyl-5-estren-17-one is stirred in 15 ml of dioxane with 1 ml of 1,5-diazabicyclo[5.4.0]undec-5-ene at room temperature. After 1.5 hours the solution is introduced into ice/water. The thus-precipitated product is filtered off, dissolved in ethyl acetate, and washed with water. Chromatography of the crude product on silica gel with hexane/acetone (0–20%) yields 300 mg of 11β-chloro-3,3-(2',2'-dimethyltrimethylenedioxy)-18-methyl-5,15-estradien-17-one, mp 144.4° C.

11β-Chloro-18-methyl-4,15-estradiene-3,17-dione 300 mg of 11β-chloro-3,3-(2',2'-dimethyltrimethylenedioxy)-18-methyl-5,15-estradien-17-one is stirred in 10 ml of acetone with 0.2 ml of semiconcentrated hydrochloric acid at room temperature. After 45 minutes, the mixture is neutralized with sodium bicarbonate solution, thereafter is concentrated under vacuum, the residue is dissolved in ethyl acetate, washed with water, and dried over sodium sulfate. After recrystallization of the crude product from acetone/hexane, 120 mg of 11β-chloro-18-methyl-4,15-estradiene-3,17-dione is obtained.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

(a) 11β-Chloro-17α-ethynyl-3,3-(2',2'-dimethyltrimethylenedioxy)-18-methyl-5,15-estradien-17β-ol Acetylene is passed for 30 minutes through a solution of 90 ml of butyllithium (15% in hexane) in 200 ml of absolute tetrahydrofuran, cooled with ice/water. This mixture is combined with 2.6 g of 11β-chloro-3,3-(2',2'-dimethyltrimethylenedioxy)-18-methyl-5,15-estradien-17-one in 30 ml of tetrahydrofuran and agitated under argon. After 30 minutes, the mixture is combined with saturated ammonium chloride solution, diluted with ethyl acetate, and washed with water. Chromatography of the crude product on silica gel with hexane/ethyl acetate (0–50%) yields 1.4 g of 11β-chloro-17α-ethynyl-3,3-(2',2'-dimethyltrimethylenedioxy)-18-methyl-5,15-estradien-17β-ol as an oil.

(b) 11β-Chloro-17α-ethynyl-17β-hydroxy-18-methyl-4,15-estradien-3-one

At room temperature, 1.4 g of 11β-chloro-17α-ethynyl-3,3-(2',2'-dimethyltrimethylenedioxy)-18-methyl-5,15-estradien-17β-ol is agitated in 20 ml of acetone with 0.5 ml of semiconcentrated hydrochloric acid. After 45 minutes, the reaction mixture is neutralized with sodium bicarbonate solution, the mixture is concentrated under vacuum, the residue is dissolved in ethyl acetate, washed with water, and dried over sodium sulfate. After recrystallization of the crude product from acetone/hexane, 700 mg of 11β-chloro-17α-ethynyl-17β-hydroxy-18-methyl-4,15-estradien-3-one is obtained, mp 202.0° C.

EXAMPLE 2

(a) 11β-Chloro-17α-chloroethynyl-3,3-(2',2'-dimethyltrimethylenedioxy)-18-methyl-15,15-estradien-17β-ol At 0° C., 12 ml of a 5% ethereal methyllithium solution is added dropwise under argon to 1.6 ml of 1,2-dichloroethylene in 12 ml of absolute ether. After 20 minutes, 650 mg of 11β-chloro-3,3-(2',2'-dimethyltrimethylenedioxy)-18-methyl-5,15-estradien-17-one in a mixture of 15 ml of ether and 5 ml of absolute tetrahydrofuran is added thereto, and the mixture is agitated at room temperature. After 15 minutes, saturated ammonium chloride solution is gently combined with the reaction mixture; the latter is diluted with ether, washed with water, and dried. Chromatography of the crude product on silica gel with hexane/acetone (0–20%) yields 520 mg of 11β-chloro-17α-chloroethynyl-3,3-(2',2'-dimethyltrimethylenedioxy)-18-methyl-5,15-estradiene-17β-ol as a frothy product.

(b) 11β-Chloro-17α-chloroethynyl-17β-hydroxy-18-methyl-4,15-estradien-3-one 400 mg of 11β-chloro-17α-chloroethynyl-3,3-(2',2'-dimethyltrimethylenedioxy)-18-methyl-5,15-estradiene-17β-ol in 15 ml of acetone is stirred with 0.5 ml of semiconcentrated hydrochloric acid for 1.5 hours at room temperature. The mixture is neutralized with sodium bicarbonate solution and exhaustively evacuated. The residue is dissolved in ethyl acetate, washed with water, and dried. Chromatography of the crude product on silica gel with hexane/acetone (0–20%) yields 230 mg of 11β-chloro-17α-chloroethynyl-17β-hydroxy-18-methyl-4,15-estradien-3-one as a frothy product.

EXAMPLE 3

(a) 11β-Chloro-3,3-(2',2'-dimethyltrimethylenedioxy)-18-methyl-17α-(1-propynyl)-5,15-estradien-17β-ol Methylacetylene is conducted for 30 minutes through a solution of 20 ml of butyllithium (15% in hexane) in 60 ml of absolute tetrahydrofuran, cooled with ice/water. The mixture is combined with 1.1 g of 11β-chloro-3,3-(2',2'-dimethyltrimethylenedioxy)-18-methyl-5,15-estradien-17-one in 10 ml of tetrahydrofuran and agitated under argon at room temperature. After one hour, saturated ammonium chloride solution is added dropwise thereto, the mixture is diluted with ethyl acetate, washed with water, and dried. The crude product is chromatographed with hexane/acetone (0–15%), thus obtaining 850 mg of 11β-chloro-3,3-(2',2'-dimethyltrimethylenedioxy)-18-methyl-17α-(1-propynyl)-5,15-estradien-17β-ol as an oil.

(b) 11β-Chloro-17β-hydroxy-18-methyl-17α-(1-propynyl)-4,15-estradien-3-one

At room temperature, 0.1 ml of semiconcentrated hydrochloric acid is added to 760 mg of 11α-chloro-3,3-(2',2'-dimethyltrimethylenedioxy)-18-methyl-17α-(1-propynyl)-5,15-estradien-17β-ol in 5 ml of acetone. After 30 minutes, the mixture is neutralized with sodium bicarbonate solution and the mixture is exhaustively concentrated under vacuum. The residue is dissolved in ethyl acetate, washed with water, and dried. Chromatography of the crude product with hexane/acetone (0–15%) yields 480 mg of 11β-chloro-17β-hydroxy-18-methyl-17α-(1-propynyl)-4,15-estradien-3-one as a frothy product.

EXAMPLE 4

17β-Acetoxy-11β-chloro-17α-ethynyl-18-methyl-4,15-estradien-3-one 700 mg of 11β-chloro-17α-ethynyl-17β-hydroxy-18-methyl-4,15-estradien-3-one in 10 ml of pyridine is reacted at room temperature with the addition of 100 mg of 4-dimethylaminopyridine with 6 ml of acetic anhydride. The mixture is introduced, after 4 hours, into ice/water which contains acetic acid. The thus-precipitated product is vacuum-filtered, dissolved in ethyl acetate, and washed with water. The crude product is chromatographed on silica gel with hexane/acetone (0–10%), thus obtaining 510 mg of 17β-acetoxy-11β-chloro-17α-ethynyl-18-methyl-4,15-estradien-3-one as a foam.

EXAMPLE 5

17β-Butyryloxy-11β-chloro-17α-ethynyl-18-methyl-4,15-estradien-3-one 300 mg of 11β-chloro-17α-ethynyl-17β-hydroxy-18-methyl-4,15-estradien-3-one in 5 ml of pyridine is stirred at room temperature with 2.0 ml of butyric anhydride and 100 mg of 4-dimethylaminopyridine. After 6 hours, the mixture is introduced into ice/water, extracted with methylene chloride, and washed with water. After chromatography of the crude product on silica gel with hexane/acetone (0–10%), 180 mg of 11β-chloro-17β-butyryloxy-17α-ethynyl-18-methyl-4,15-estradien-3-one is obtained as an oil.

EXAMPLE 6

11β-Chloro-17α-ethynyl-17β-heptanoyloxy-18-methyl-4,15-estradien-3 one 350 mg of 11β-chloro-17α-ethynyl-17β-hydroxy-18-methyl-4,15-estradien-3-one in 4 ml of pyridine is combined at room temperature with 2 ml of enanthic acid anhydride and 60 mg of 4-dimethylaminopyridine. After 20 minutes, the solution is introduced into ice/water, extracted with methylene chloride, and washed with water. Chromatography of the crude product on silica gel with hexane/acetone (0–8%) yields 230 mg of 11β-chloro-17α-ethynyl-17β-heptanoyloxy-18-methyl-4,15-estradien-3-one as an oil.

EXAMPLE 7

11β-Chloro-17α-chloroethynyl-18-methyl-17β-propionyloxy-4,15-estradien-3-one 200 mg of 11β-chloro-17α-chloroethynyl-17β-hydroxy-18-methyl-4,15-estradien-3-one in 4 ml of pyridine is stirred at room temperature with 1.5 ml of propionic anhydride and 20 mg of 4-dimethylaminopyridine. After 4 hours, the solution is introduced into ice/water. The thus-precipitated product is vacuum-filtered, dissolved in methylene chloride, washed with water, and dried. After chromatography of the crude product on silica gel with hexane/acetone (0–8%), 150 mg of 11β-chloro-17α-chloroethynyl-18-methyl-17β-propionyloxy-4,15-estradien-3-one is obtained as an oil.

EXAMPLE 8

17β-Acetoxy-11β-chloro-18-methyl-17α-(1-propynyl)-4,15-estradien-3-one 280 mg of 11β-chloro-17β-hydroxy-18-methyl-17α-(1-propynyl)-4,15-estradien-3-one in 4 ml of pyridine is stirred with 2 ml of acetic anhydride and 30 mg of 4-dimethylaminopyridine at room temperature. After 3 hours, the solution is introduced into ice/water. The thus-precipitated product is vacuum-filtered, dissolved in ethyl acetate, washed with water, and dried. Chromatography of the crude product on silica gel with hexane/acetone (0–10%) yields 175 mg of 17β-acetoxy-11β-chloro-18-methyl-17α-(1-proponyl)-4,15-estradien-3-one as a foam.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. An 11β-chloro-Δ¹⁵-steroid of the formula

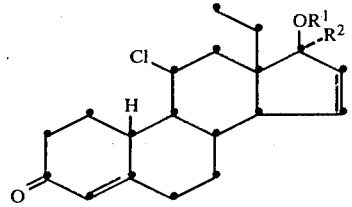

wherein
R¹ is hydrogen or an acyl group derived from a C₁₋₁₅-hydrocarbon carboxylic acid, and
R² is ethynyl, chloroethynyl, or propynyl.

2. A compound of claim 1 wherein R¹ is H.
3. A compound of claim 1 wherein R¹ is acyl.
4. A compound of claim 1 wherein R² is ethynyl.

5. A compound of claim 1 wherein $R^2$ is chloroethynyl.

6. A compound of claim 1 wherein $R^2$ is propynyl.

7. A compound of claim 1 wherein $R^1$ is $C_{1-15}$-alkanoyl.

8. 11β-Chloro-17α-ethynyl-17β-hydroxy-18-methyl-4,15-estradien-3-one, a compound of claim 1.

9. 11β-Chloro-17α-chloroethynyl-17β-hydroxy-18-methyl-4,15-estradien-3-one, a compound of claim 1.

10. 11β-Chloro-17β-hydroxy-18-methyl-17α-(1-propynyl)-4,15-estradien-3-one, a compound of claim 1.

11. 17β-Acetoxy-11β-chloro-17α-ethynyl-18-methyl-4,15-estradien-3-one, a compound of claim 1.

12. 17β-Butyryloxy-11β-chloro-17α-ethynyl-18-methyl-4,15-estradien-3-one, a compound of claim 1.

13. 11β-Chloro-17α-ethynyl-17β-heptanoyloxy-18-methyl-4,15-estradien-3-one, a compound of claim 1.

14. 11β-Chloro-17α-chloroethynyl-18-methyl-17β-propionyloxy-4,15-estradien-3-one, a compound of claim 1.

15. 17β-Acetoxy-11β-chloro-18-methyl-17α-(1-propynyl)-4,15-estradien-3-one, a compound of claim 1.

16. A pharmaceutical composition comprising a progestationally effective amount of an 11β-chloro-$\Delta^{15}$-compound of claim 1 and a pharmacologically acceptable carrier.

17. An orally administrable composition of claim 16 containing 0.01–0.5 mg of the 11β-chloro-$\Delta^{15}$-compound.

18. A composition of claim 16 which is a parenteral solution containing 1–100 mg of the 11β-chloro-$\Delta^{15}$-compound per milliliter of solution.

19. A method of achieving a progestational effect in a patient comprising administering to the patient an effective amount of a compound of claim 1.

* * * * *